(12) United States Patent
Breul et al.

(10) Patent No.: US 9,029,390 B2
(45) Date of Patent: May 12, 2015

(54) ORAL COMPOSITION CONTAINING AN ANTIPLATELET AGENT OF THE THIENOPYRIDINE FAMILY IN THE FORM OF FREE BASE

(75) Inventors: Thierry Breul, Frontignan (FR); Claude Laruelle, Villeneuve-Loubet (FR)

(73) Assignee: CLL Pharma, Nice Cedex (FR)

( * ) Notice: Subject to any disclaimer, the term of this patent is extended or adjusted under 35 U.S.C. 154(b) by 29 days.

(21) Appl. No.: 12/737,183

(22) PCT Filed: Jun. 15, 2009

(86) PCT No.: PCT/FR2009/000707
§ 371 (c)(1),
(2), (4) Date: Dec. 16, 2010

(87) PCT Pub. No.: WO2009/153448
PCT Pub. Date: Dec. 23, 2009

(65) Prior Publication Data
US 2011/0123606 A1    May 26, 2011

(30) Foreign Application Priority Data
Jun. 16, 2008    (FR) .................................... 08/03358

(51) Int. Cl.
| | |
|---|---|
| C08L 77/06 | (2006.01) |
| C08L 51/06 | (2006.01) |
| C08K 7/24 | (2006.01) |
| C08K 3/04 | (2006.01) |
| A61K 31/4365 | (2006.01) |
| A61K 9/48 | (2006.01) |

(52) U.S. Cl.
CPC ........... *A61K 31/4365* (2013.01); *A61K 9/4858* (2013.01)

(58) Field of Classification Search
None
See application file for complete search history.

(56) References Cited

U.S. PATENT DOCUMENTS

| | | | |
|---|---|---|---|
| 6,383,471 B1 * | 5/2002 | Chen et al. ...................... | 424/45 |
| 2003/0215496 A1 * | 11/2003 | Patel et al. ..................... | 424/452 |
| 2007/0243243 A1 * | 10/2007 | Goldsmith et al. ........... | 424/451 |
| 2008/0125477 A1 * | 5/2008 | Singh et al. ................... | 514/414 |
| 2008/0214599 A1 | 9/2008 | Brandt | |

(Continued)

FOREIGN PATENT DOCUMENTS

| | | |
|---|---|---|
| EP | 1 621 200 | 2/2006 |
| FR | 2 782 455 | 2/2000 |
| JP | 7-242568 | 9/1995 |

(Continued)

OTHER PUBLICATIONS

Ansel (Pharmaceutical Dosage Forms and Drug Delivery Systems 1999, 7th Edition, Lippincott Williams & Wilkins pp. 179, 183 and 185).*

(Continued)

*Primary Examiner* — Ernst V Arnold
(74) *Attorney, Agent, or Firm* — Nixon & Vanderhye P.C.

(57) ABSTRACT

The invention relates to non hemolytic compositions containing an antiplatelet agent such as clopidogrel or ticlopidine; these compositions being characterized in that the antiplatelet agent is in the form of free base, and the composition contains at least one hydrophilic non ionic surfactant. The invention relates also a galenic form, a method of preparation of thereof, as well as therapeutic uses of thereof, especially in patients who suffer from undesirable effects related to hemolysis and/or gastrointestinal acidity.

34 Claims, 6 Drawing Sheets

Dissolution test in the simulated intestinal fluid FaSSIF at 37°C
for formulations 5-8 compared to a solution containing Plavix®

« % clopid dissous » means « % of dissolved clopidogrel »; « temps » means : « time ».
- EL = formulation 1 containing Cremophor®EL ;
- HS-15 = formulation 2 containing solutol® HS-15 ;
- RH-40 = formulation 3 containing Cremophor®RH-40 ;
- TPGS = formulation 4 containing Cremophor®RH-40 and vitamin E-TPGS

(56) References Cited

U.S. PATENT DOCUMENTS

2009/0062240 A1    3/2009  Edgar
2010/0292268 A1*  11/2010  Mosher et al. ................ 514/301

FOREIGN PATENT DOCUMENTS

| | | |
|---|---|---|
| WO | 2004/074215 | 9/2004 |
| WO | 2007/024472 | 3/2007 |
| WO | 2008/134601 | 11/2008 |

OTHER PUBLICATIONS

International Search Report for PCT/FR2009/000707, mailed Oct. 21, 2009.

Database WPI Week 199546, Thomson Scientific, London, GB; An 1995-355195.

Zupancic et al, "Preformulation Investigation of Some Clopidogrel Addition Salts", Acta Chim. Slov. 2010, 57, 376-385.

* cited by examiner

Figure 1 : AGL hemolysis test for formulations 1-4 compared to Plavix® at a clopidogrel concentration of 10 µg/ml in Patient blood n°1

DO : optical density ; « temps » = time (minute)

- EL = formulation 1 containing Cremophor®EL ;
- HS-15 = formulation 2 containing solutol® HS-15 ;
- RH-40 = formulation 3 containing Cremophor®RH-40 ;
- TPGS = formulation 4 containing Cremophor®RH-40 and vitamin E-TPGS

Figure 2: AGL hemolysis test for formulations 1-4 compared to Plavix® at a clopidogrel concentration of 10 µg/ml in Patient blood n°2

DO : optical density ; « temps » = time (minute)

- EL = formulation 1 containing Cremophor®EL ;
- HS-15 = formulation 2 containing solutol® HS-15 ;
- RH-40 = formulation 3 containing Cremophor®RH-40 ;
- TPGS = formulation 4 containing Cremophor®RH-40 and vitamin E-TPGS

Figure 3 :   AGL hemolysis test for formulations 1-4 compared to Plavix® at a clopidogrel concentration of 16.7 µg/ml DO : optical density ; « temps » = time (minute)

- EL = formulation 1 containing Cremophor®EL ;
- HS-15 = formulation 2 containing solutol® HS-15 ;
- RH-40 = formulation 3 containing Cremophor®RH-40 ;
- TPGS = formulation 4 containing Cremophor®RH-40 and vitamin E-TPGS

Figure 4 : AGL hemolysis test for formulations 1-4 at a clopidogrel concentration of 200µg/ml compared to Plavix® at a clopidogrel concentration of 16.7µg/ml DO : optical density ; « temps » = time (minute)

- EL for the formulation 1 containing Cremophor®EL ;
- HS-15 for the formulation 2 containing solutol® HS-15 ;
- RH-40 for the formulation 3 containing Cremophor®RH-40 ;
- TPGS for the formulation 4 containing Cremophor®RH-40 and vitamin E-TPGS

Figure 5 : Dissolution test in the simulated intestinal fluid FaSSIF at 37°C for formulations 5-8 compared to a solution containing Plavix®

« % clopid dissous » means « % of dissolved clopidogrel »; « temps » means : « time ».

- EL = formulation 1 containing Cremophor®EL ;
- HS-15 = formulation 2 containing solutol® HS-15 ;
- RH-40 = formulation 3 containing Cremophor®RH-40 ;
- TPGS = formulation 4 containing Cremophor®RH-40 and vitamin E-TPGS

Figure 6 : Dissolution test in the simulated intestinal fluid FeSSIF at 37°C for formulations 5-8 compared to that of a solution containing Plavix®

« % clopid dissous » means « % of dissolved clopidogrel »; « temps » means : « time ».

- EL = formulation 1 containing Cremophor®EL ;
- HS-15 = formulation 2 containing solutol® HS-15 ;
- RH-40 = formulation 3 containing Cremophor®RH-40 ;
- TPGS = formulation 4 containing Cremophor®RH-40 and vitamin E-TPGS

ORAL COMPOSITION CONTAINING AN ANTIPLATELET AGENT OF THE THIENOPYRIDINE FAMILY IN THE FORM OF FREE BASE This application is the U.S. national phase of International Application No. PCT/FR2009/000707, filed 15 Jun. 2009, which designated the U.S. and claims priority to French Application No. 08/03358, filed 16 Jun. 2008, the entire contents of each of which are hereby incorporated by reference.

The invention refers to oral formulations containing an antiplatelet agent of the thienopyridines family in the form of free base, to a method of preparation of those, and to their use in the treatment or the prevention of pathologies related to atherothrombosis.

The atherosclerosis is the most frequent cause of thrombotic cardio- and cerebrovascular diseases, and represents the most probable cause of premature morbidity and mortality in the last 40 years. According to the studied population and the method used, the prevalence of arterial pathologies is estimated between 25 and 60%, and the one of myocardial infarction to 2% (Touze E and Al. Arch Badly Vaiss Heart. 2005; 98 (4): 15-30).

Among the treatment prescribed for the prevention of atherothrombosis (myocardial infarction, cerebral vascular accident, vascular death), one can find antiplatelet agents belonging to the thienopyridines family such as ticlopidine marketed under the name Ticlid®, and clopidogrel marketed under the name of Plavix®; these 2 molecules being described respectively in patents FR 7 303 503 and EP 281 459. A more recent thienopyridine, prasugrel, is described in application JP 06 041139 A, is not marketed yet, but is shown in several studies as having an antiplatelet activity (Wiviott S D and Al, 2005, Circulation, 111 (25): 3366-73).

Active molecule is in the form of hydrochloride salt in Ticlid® and in the form of hydrogenosulfate salt in Plavix®. No oral formulation of clopidogrel or ticlopidine in the form of free base is marketed so far.

Patents EP 099 802, EP 281 459 and U.S. Pat. No. 4,847,265 describe compositions containing clopidogrel or one of its pharmaceutically acceptable salts to be administered by parenteral route and are presented in the form of injectable aqueous solutions. It can be deduced that this kind of formulation which contains a clopidogrel salt dissolved in an isotonic solvent is not appropriate for an administration by oral route, since clopidogrel is degraded by an oxidation reaction in presence of water. Moreover, the compositions obtained cannot be preserved in a stable form for more that one month. One can add that this kind of solution for which the pH is lower than 2, would probably cause, in case of an administration by oral route, stomach irritations due to its very acidic pH.

Patent application WO 97/17064 describes a freeze-dried form for parenteral or by catheter administration which contains mannitol and alanine in addition to clopidogrel or one of its salts.

Patent application WO 00/10534 describes an injectable aqueous pharmaceutical composition containing clopidogrel or ticlopidine; this composition containing additionally a basic agent such as disodium phosphate, and the two surface-active agents Pluronic® F680 (Poloxamer 188) and Solutol® HS15; the first one being used as aggregation inhibitor. The active ingredient is used preferably in the form of salt and is exemplified only under this form. Starting from a freeze-dried product, one can reconstitute a solution with an aqueous solvent then giving a micellar clopidogrel solution with a pH higher than 3. According to the Applicant, this would have the advantage to abolish the problem of auto-aggregation of clopidogrel due to the use of the two surface-active agents. However, the described composition requires, before its administration, an extemporaneous reconstitution by dissolution of the freeze-dried product in order to limit the degradation of clopidogrel in presence of water. According to this prior art, one can notice that the preparation of a liquid form containing a pharmaceutically acceptable salt of clopidogrel or ticlopidine appears to be fastidious because of physicochemical properties of these active ingredients and in particular of their chemical instability in the presence of water.

Applications WO 04/026879 A and WO 06/044548 A describe compositions containing clopidogrel in the form of free base. WO 04/026879 A describes an amorphous form of clopidogrel, as well as a method of preparation of a complex by co-dissolution of the clopidogrel free base (either directly in this form, or in situ starting from the addition of an acid to a solution of clopidogrel bisulfate) and of a N-vinyl-2-pyrrolidone polymer, then followed by a step of solvent evaporation to obtain a dry solid residue. Application WO 06/044548 describes a solid premix containing clopidogrel in the form of free base; the latter being adsorbed on a carrier chosen among sugars, disaccharides and cellulose derivatives. The galenic form obtained according to this invention is a tablet, a powder, a sachet and the like. The objective is, according to the Applicant, to improve the fluidity of clopidogrel in the form of free base, and also to allow a better homogeneity and to facilitate the premix preparation. According to the Applicant, this kind of formulation makes it possible to improve stability, solubility, the implementation of its preparation and to reduce its hygroscopicity. However, these two PCT applications by no means refer to a reduction of undesirable effects such as the hemolysis and gastric irritation linked to the use of these antiplatelet agents.

The administration of Ticlid® or Plavix® frequently causes undesirable effects such as stomach irritations and even bleedings. They give aqueous solutions having a pH lower than 2, which is incompatible with a good gastric safety by oral administration. On this purpose, it is mentioned in the notice of Ticlid® the following recommendation: "to take during the meal in order to reduce digestive disorders". For Plavix®, the safety was studied on over 42,000 patients; over 9000 of them being treated during one year or more. The notable undesirable effects, which were recorded during the study CAPRIE, include in particular, among patients who received clopidogrel, a frequency of 2.0% gastro-intestinal bleedings having required a hospitalization in 0.7% of the cases. Moreover, the ticlopidine administration is even contraindicated in patients suffering of gastroduodenal ulcer.

Among other undesirable effects linked to the administration of ticlopidine or clopidogrel, one can find also hemorrhagic events and hematologic diseases; some of them being related to hemolysis.

In case of Ticlid®, and in the majority of the cases, these accidents occur during the first 3 months of treatment, and a biological monitoring (blood test) is necessary during this period (generally every 15 days). The hematologic toxicity is the fall of the rate of white globules, platelets or red cells (anaemia) or of the 3 together; the latter case being extremely serious. If the numeration of the blood cells is modified, the treatment must be stopped. In the same way, digestive haemorrhages as well as those ophthalmologic, otorhinolaryngologic (ORL), cerebral and meninx require to stop the treatment.

Among the hematologic disorders observed after the administration of clopidogrel, is found the thrombotic microangiopathy (TMA) which indicates some endothelium lesions of small arteries and capillaries; these lesions being common to two clinical syndromes which associate thrombopenia and hemolytic anaemia. Hemolytic anaemia is regarded as a severe anaemia, the hemolysis is intravascular and the microangiopathic aspect of this anaemia is observed by the presence of many deformations of the red cells. Cases of TMA were reported after administration of ticlopidine or clopidogrel, causing the uremic hemolytic syndrome (HUS): (Anderson F. et al. Heart, 2004, 90:9, 57; Medina P J et al., Curr. Opin. Hematol, 2001, 8: 5,286-93).

In addition to the TMA, one can find as hemolytic pathology the favism which corresponds to a deficiency in G6PD (glucose-6-phosphate dehydrogenase) which is a red cell enzyme. It was shown that a deficiency of this enzyme causes a hemolysis or destruction of the red cells leading to anaemia. This deficiency in G6PD is frequent in some populations, for example, it affects more than 10% of the afro-americans and is particularly widespread among Mediterranean people, appearing by crisis of acute hemolysis. The deficit in G6PD is most common of the enzymatic deficiency in men, one estimates at more than 400 million the number of people affected by a deficit in G6PD.

According to what was previously exposed, there is a need to develop a formulation containing an antiplatelet agent such as clopidogrel or ticlopidine, which can allow to notably reducing undesirable effects such as hemolysis, stomach irritation and/or bleeding.

The Applicant has set up a formulation having a strong potential to reduce some of the undesirable effects presented previously, and in particular hemolysis. This new composition makes it possible to obtain a neutral pH after its dilution in water. Lastly, this new composition has the advantage to make absorption independent of food intake, in contrast to the clopidogrel in the form of hydrogenosulfate salt for which a food effect exists. Indeed, variations of absorption according to fasted or fasting states were shown from a study carried out on healthy volunteers to who clopidogrel in the form of hydrogenosulfate salt was administered (Nigori, R V S et al., Arzneimittel-Forschung, 2006, vol. 56, $n^o$ 11 pp. 735-739).

The present Invention has the objective to present non-hemolytic oral pharmaceutical composition containing an antiplatelet agent chosen among the thienopyridine family, which displays a pH near to neutrality after its dilution in water; this formulation is characterized in that the antiplatelet agent is in the form of free base, and that the formulation contains additionally at least a hydrophilic non-ionic surface active agent. The expression "near to neutrality" refers to a pH ranging between 5 and 8 after dilution in water. The Applicant has noticed that this new formulation alleviates the solubility problem of Plavix®, since the latter contains the clopidogrel in the form of salt which requires a very low pH to be dissolved; this requirement being unnecessary anymore for the formulations of the Invention. Moreover, the new formulations have the advantage to offer a dissolution profile very similar in fasting and fed simulated intestinal fluids, and therefore do not present food effect.

Among the antiplatelet agents, one finds clopidogrel, ticlopidine and prasugrel; the clopidogrel being preferred within the framework of the Invention.

The Applicant indeed showed that in the case of the clopidogrel the use of the free base and not of hydrogenosulfate salt (such as in Plavix®), in the presence of a certain type of surfactant, does not only make possible to dissolve the free base, but also allows to reduce undesirable effects related to the use of hydrogenosulfate salt of clopidogrel such as hemolysis or gastric acidity.

During this study, the Applicant noted that among the numerous marketed surfactants which are available, a particular category of hydrophilic non-ionic surfactants allow the dissolution of the poorly hydrophilic free base in suitable conditions. In addition to this activity, the Applicant showed during in vitro tests that surprisingly this composition has the ability to reduce notably hemolysis compared to Plavix®.

According to the invention, the hydrophilic non-ionic surfactants are selected among the ones—or a mixture—for which the hydrophilic/lipophilic balance is higher than 10. In this respect, one can refer to the handbook "Handbook of Surfactants" by M. R. Porter, Blackie &Sons Editions, $2^{nd}$ Edition, 1994.

According to an advantageous provision, hydrophilic non-ionic surfactants are the Cremophor® EL, Cremophor® RH-40, Solutol® HS-15 or the mixture of Cremophor® RH-40 and vitamin E/TPGS®. According to a even more advantageous provision, they are the Cremophor®RH-40 or the mixture Cremophor®RH-40 and vitamin E/TPGS®. Cremophor® EL and Cremophor® RH-40 are emulsifiers sold by BASF; they correspond to polyoxyethylene castor oils; Solutol® HS-15 sold by BASF corresponds to polyoxyethylene esters of 12-hydroxystearic acid; vitamin E/TPGS® corresponds to tocopheryl polyethylene glycol succinate.

Optionally, the composition can incorporate preservatives and/or antioxidants such as for example the butyl-hydroxyanisole (BHA) butyl-hydroxytoluene (BHT), acid ethylene tetracetic diamine (EDTA) or its salts, the methyl or propylparabens, salts of the derivatives of 10-para hydroxybenzoïque acid.

In addition, the Applicant showed that during the in vitro studies, the new formulations display surprisingly a dissolution profile of the active ingredient independent to a food effect. Indeed, tests carried out in simulated intestinal fluids which reproduce the fasted intestinal bowl (FaSSIF) and fed intestinal bowl (FeSSIF) do not show any difference on the level of dissolution of the active ingredient between these two media. These results contrast to those obtained with the reference Plavix® for which clopidogrel under hydrogenosulfate salt dissolves differently in FaSSIF and in FeSSIF media; this food effect being already described in the publication of Nigori et al. presented previously.

According to a particular provision, the pharmaceutical composition of the Invention is characterized by a solubility of the antiplatelet agent higher than 70 mg/ml in an intestinal fluid according to the USP pharmacopeia XXI at a pH=7.5 and a temperature of 37° C.

According to another particular provision, the pharmaceutical composition of the Invention is characterized by a dissolution of the antiplatelet agent higher than 95% in the FeSSIF or FaSSIF simulated intestinal fluids within 30 minutes at a temperature of 37° C. and under shaking of 50 rpm.

The invention also has also as object a pharmaceutical composition such as previously described under the form of a capsule; this capsule containing a dosage of clopidogrel or ticlopidine ranging between 5 and 600 mg; preferred dosage being of 300 mg which corresponds to the loading dosage for patients suffering from acute coronary syndrome; the most preferred dosage being 75 mg of clopidogrel which corresponds to that of Plavix® which is marketed and prescribed for the majority of patients suffering of atherothrombosis.

The capsule according to the Invention contains preferably, in addition to the antiplatelet agent, at least one hydrophilic non ionic surfactant. According to an advantageous provision, the capsule contains 75 mg of clopidogrel under the form of free base and between 250 to 600 mg of hydrophilic non ionic surfactant chosen among Cremophor®RH-40, Solutol® HS 15, Cremophor® EL and a mixture of Cremophor® RH-40 and vitamin E/TPGS. According to a provision even more advantageous, the capsule according to the invention contains 75 mg of clopidogrel under the form of free base associated to 290 mg of Cremophor®RH-40 or associated to the mixture of 287 mg Cremophor® RH-40 and 3 mg of vitamin E/TPGS.

The capsule of the Invention will be preferentially made up out of soft or hard gelatin or hydropropylmethylcellulose (HPMC), and can be sealed or not.

Advantageously, one can use a capsule of size 1 or size 0. The capsule of smaller size 1 is particularly preferred, since it is appropriate particularly to patients having difficulties to swallow capsules of bigger size.

Moreover, one objective of the Applicant is to provide a solubilisation process, which is simple to implement and does not require other equipment that the one classically used in pharmaceutical laboratories.

Therefore, the present Invention describes a solubilisation process of a pharmaceutical composition according to the invention, including the following steps:
(a) at least one hydrophilic non ionic surfactant is heated at a temperature ranging between 30° C. and 60° C.;
(b) the active principle is dissolved under agitation at a temperature ranging between 30° C. and 60° C. in the preceding hydrophilic non ionic surfactant(s).

The Applicant has noticed that prior to the addition of the active principle, it was preferable to heat the surfactant(s) in order to decrease their viscosity and to accelerate the dissolution of the active principle.

Another object of the Invention is a preparation process of a capsule as previously described, including the following steps:
(a) at least one hydrophilic non ionic surfactant is heated at a temperature ranging between 30° C. and 60° C.;
(b) the active principle is dissolved under agitation at a temperature ranging between 30° C. and 60° C. in the preceding hydrophilic non ionic surfactant(s);
(c) optionally the mixture obtained from step (b) is cooled down at room temperature;
(d) optionally the mixture obtained from step (c) is heated at a temperature ranging between 30° C. and 45° C.;
(e) the mixture obtained from step (d) is transferred into the capsules.

According to a particular disposition of the Invention, this type of non hemolytic formulation can be used in patients treated for pathologies related to atherothrombosis and who met undesirable effects during their treatment with usual antiplatelet agent medicine.

Advantageously, the formulation of the Invention is provided for patients who are likely to meet undesirable effects related on hemolysis, or gastrointestinal acidity when the antiplatelet agent such as the clopidogrel or ticlopidine is used in the form of salt.

According to another advantageous provision, the patients treated by the formulation of the Invention are the ones who are defective in the glucose-6-phosphate dehydrogenase (G6PG), or patients suffering from hematologic disorders such as the thrombotic microangiopathy, or patients suffering from the hemolytic uremic syndrome.

According to another advantageous provision, the patients treated by the composition of the Invention are the ones suffering from gastroduodenal ulcer or gastrointestinal bleedings.

The invention will be better understood by the following examples which refer to non hemolytic formulations of clopidogrel free base and to various tests (hemolysis, solubility, dissolution and pH) in which new formulations are compared to Plavix®; and which are associated to the following figures.

The following examples are given to illustrate the invention and do not constitute in any manner a limitation of it.

EXAMPLE 1

Test of Hemolysis. Comparison Between the Formulations of the Invention and Plavix®

In order to determine the hemolytic potential of clopidogrel, a hemolysis test was performed on Plavix® which contains clopidogrel in the form of hydrogenosulfate salt and on the formulations according to the Invention containing of clopidogrel in the form of free base.

Formulations 1 to 4 according to the invention are described in the following Table 1: each one contains 75 mg of clopidogrel free base and identical amount of hydrophilic non ionic surfactant; this one being different between them.

The tablet Plavix® contains 97.87 mg of clopidogrel hydrogenosulfate (75 mg of clopidogrel free base) and the following carriers: anhydrous lactose, modified corn starch, macrogol, microcrystalline cellulose, hydrogenated castor oil, titanium dioxide, red ferric oxide and carnauba wax.

TABLE 1

Formulations of size 0 capsules according to the invention

| Formulation | Clopidogrel free base (mg) | Hydrophilic non ionic surfactant (name, mg) | | Total amount (mg) |
|---|---|---|---|---|
| 1 | 75 | Cremophor ® EL | 525 | 600 |
| 2 | 75 | Solutol ® HS-15 | 525 | 600 |
| 3 | 75 | Cremophor ® RH-40 | 525 | 600 |
| 4 | 75 | Cremophor ® RH-40 Vitamin E/TPGS | 519.75 5.25 | 600 |

Hemolysis Test (AGL)

This test used here is the acidified glycerol lysis test as described in A. Zanella et al. (British Newspaper of Haematology, (1980) 45.481-6). This consists in measuring in an acidified medium the in vitro osmotic strength of red globules by measuring the optical density (OD). The cellular lysis is determined by monitoring the evolution of the turbidity which occurs when the integrity of the plasmic membrane is altered. The hemolysis is rated when the OD observed after 30 minutes is reduced by half or less from the initial one (OD 50%).

AGL tests allow also to detect hereditary and autoimmune hemolytic anaemia [P. H. B. Bolton-Maggs et al. (2004) "Guidelines for the diagnosis and management of hereditary spherocytosis" British Newspaper of Haematology, 126,455-474].

Experimental Protocol

Reagents Used:

Glycerol reagent: dilution of 1.1 ml of glycerol in 15 ml of PBS and in 50 ml of distilled water;

Phosphate buffer: the phosphate buffer titrisol is diluted in 500 ml of water and the pH adjusted to 6.85;

PBS buffer: 8.1 g of NaCl is diluted in 900 ml of water and in 100 ml of phosphate buffer (pH 6.85).

The blank cuve contains 1 ml of PBS and 2 ml of glycerol reagent. The sample cuve contains 5 ml of formulation 1, 2, 3 or 4 or Plavix® to which 20 µl of blood is added. Incubation is allows for 30 minutes. To the sample cuve is added 1 ml of the previous solution, and 2 ml of glycerol reagent. The highest concentration of clopidogrel is 15 µg/ml; this corresponds to a dosage of 75 mg in 5 litres of blood. Therefore, this concentration will be reduced when the PBS buffer is added. The monitored parameter is the optical density (OD) at 625 nm which is the optimal wavelength when the highest discrepancy is obtained between intact and lysed cells.

Tests Carried Out:

Concentration of 10 µg/ml Clopidogrel Free Base

The test was carried out on blood from two selected patients. An aliquot of 20 µl of blood is added to solution of formulation 1, 2, 3, 4 or Plavix® in order to obtain a clopidogrel free base concentration of 10 µg/ml. Each test is duplicated. The results are presented in FIG. 1 (patient blood n° 1) and in FIG. 2 (patient blood n° 2) in which the average of the duplicate test is reported.

Figure 1:
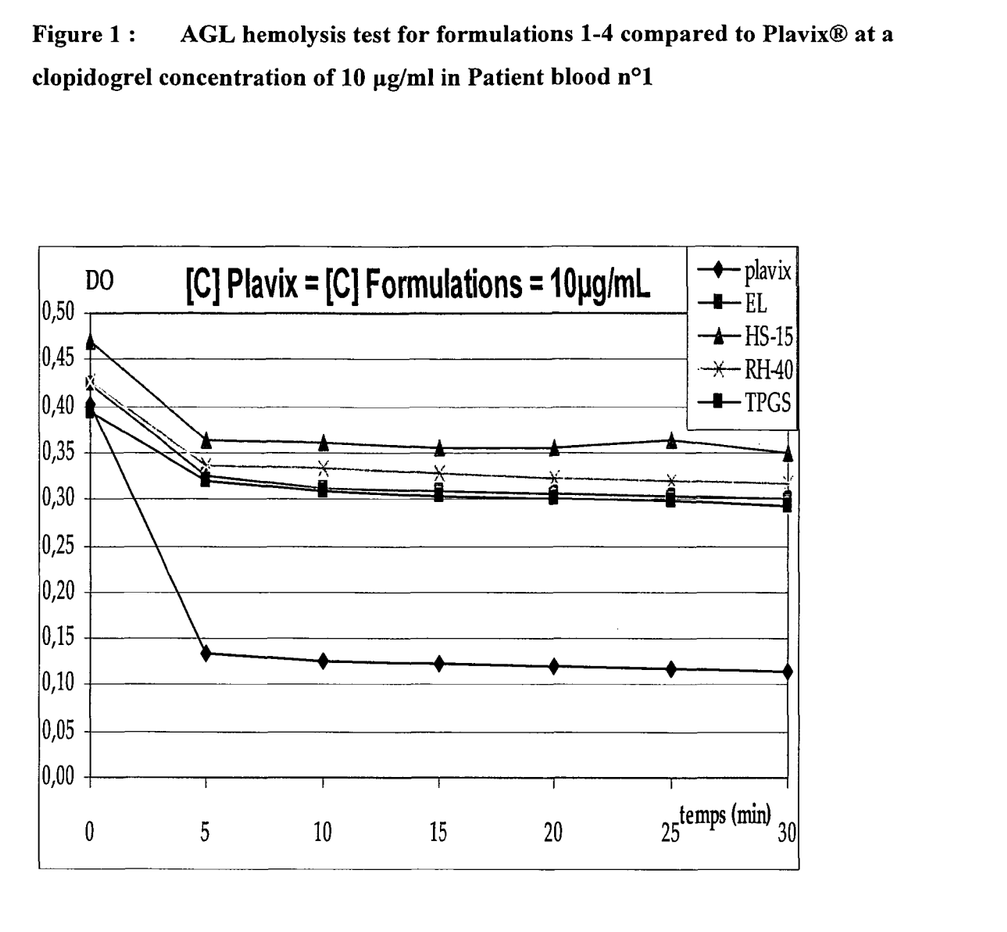
FIG. 1 shows the results of hemolysis by using the acidified glycerol lysis test (said also "test AGL") on the blood of patient N° 1, during which formulations 1 to 4 of the Invention are compared to Plavix®; all formulations having a concentration of 10 µg/ml of clopidogrel.
Figure 2:
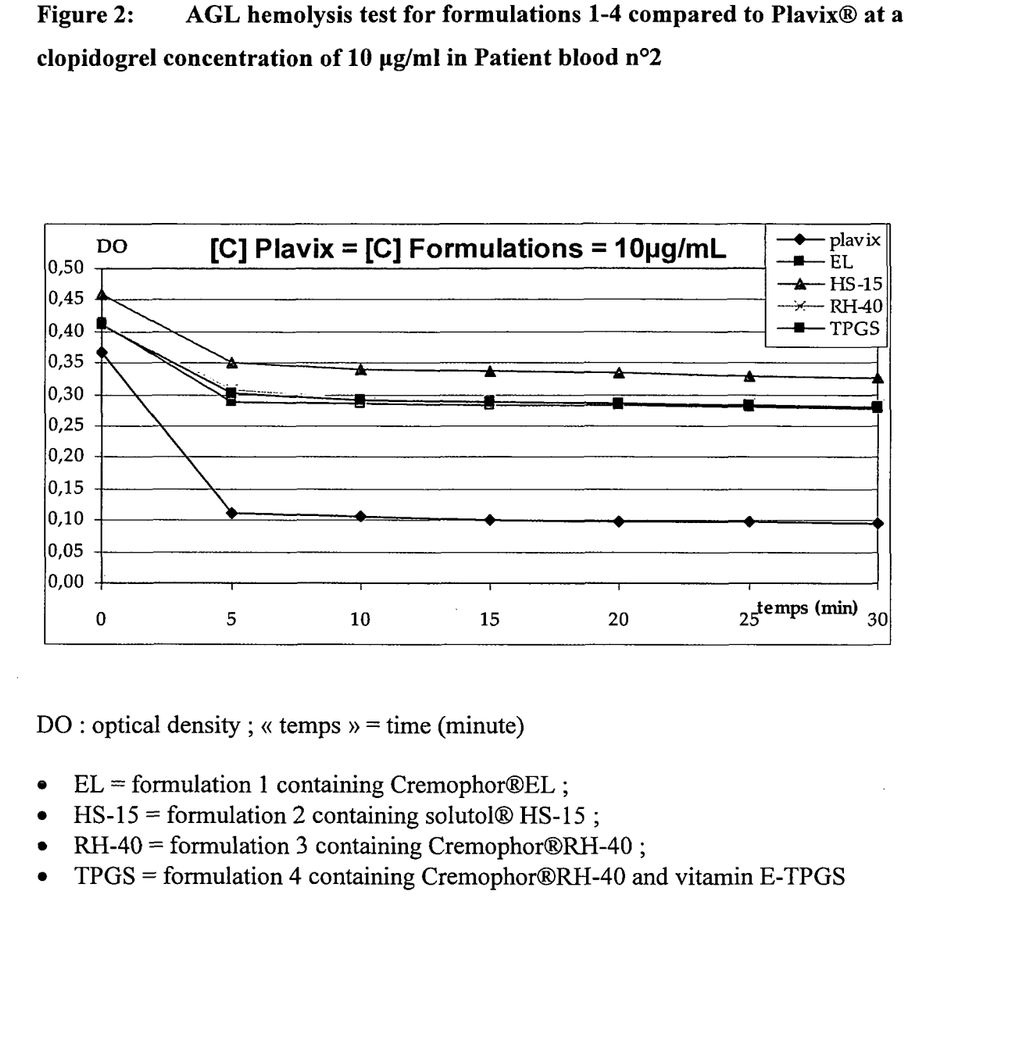
FIG. 2 shows the results of hemolysis as performed in FIG. 1 on the blood of patient N° 2.

For the patient blood n° 1, one observes that the OD loss of more than 50% is obtained for Plavix®, indicating an important hemolysis, whereas the OD loss for formulations 1 to 4 ranges between 19% and 29%, indicating a much reduced hemolysis. Similar results were obtained when the test was repeated on patient blood n° 2: more than 50% OD loss for Plavix® versus the range between 25% and 32% for formulations 1 to 4 of the Invention.

Concentration of 16.7 µg/ml of Clopidogrel Free Base

Figure 3:
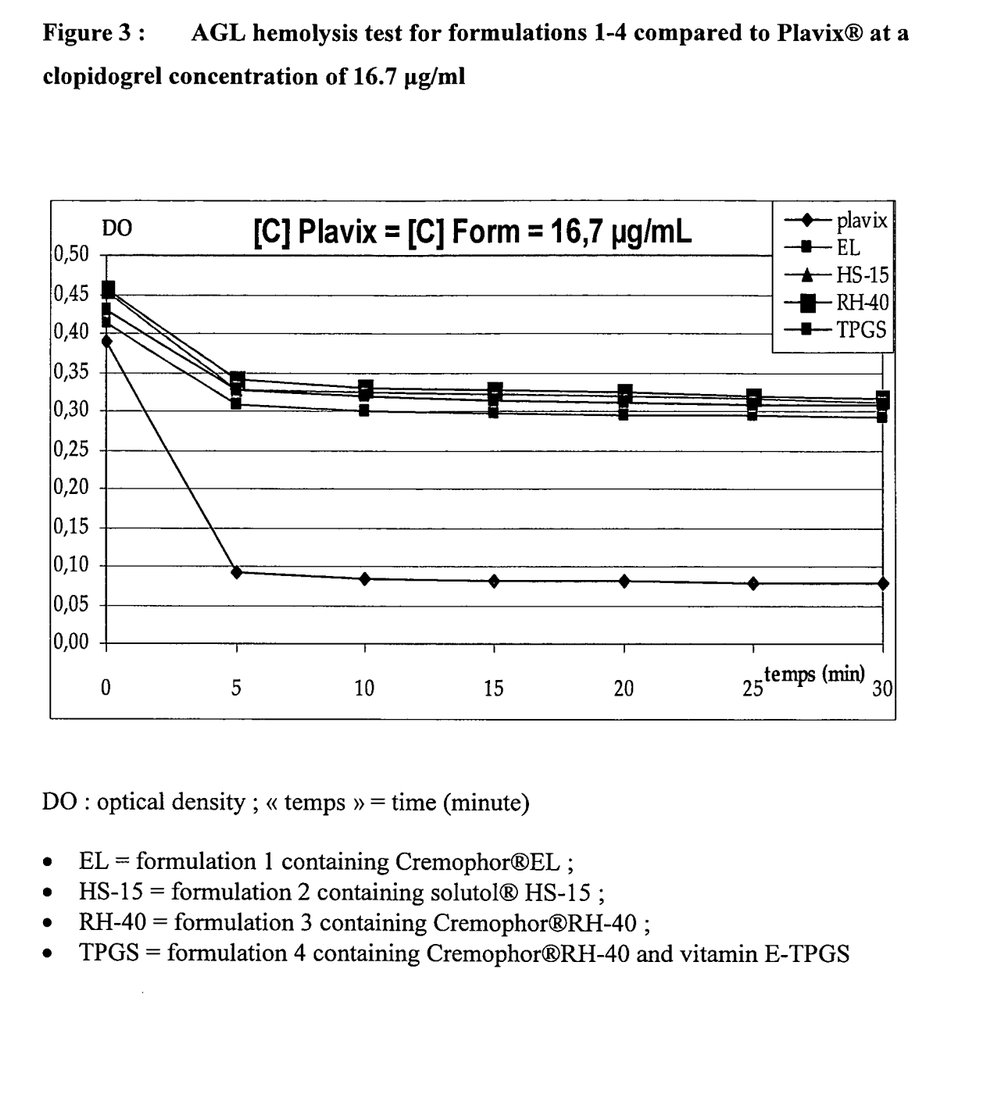
FIG. 3 corresponds to the same test as that of FIG. 1 with a concentration of clopidogrel of 16.7 µg/ml for all formulations including Plavix®.

Aliquots of 20 µl of patient blood are added either to a solution of Plavix®, or to one of formulation 1 to 4 in order to obtain a concentration of 16.7 µg/ml clopidogrel free base. Each test is duplicated. Results are presented in the FIG. 3. We notice that the results are very similar to those obtained at a lower concentration of 10 µg/ml clopidogrel free base: the OD loss is higher than 50% for Plavix®, indicating an important hemolysis, whereas the OD loss is much reduced for formulations 1 to 4 (between 29% and 32%), indicated a reduction of hemolysis.

Concentration of 200 µg/ml Clopidogrel Free Base in Formulations 1 to 4

In order to determine the amount in clopidogrel from which an important hemolysis is observed for the formulations of the Invention, tests were carried out for concentration of clopidogrel free base of 100 µg/ml (results not shown) and of 200 µg/ml, while keeping a much lower amount in clopidogrel for the solution containing Plavix® (16.7 µg/ml).

Figure 4:
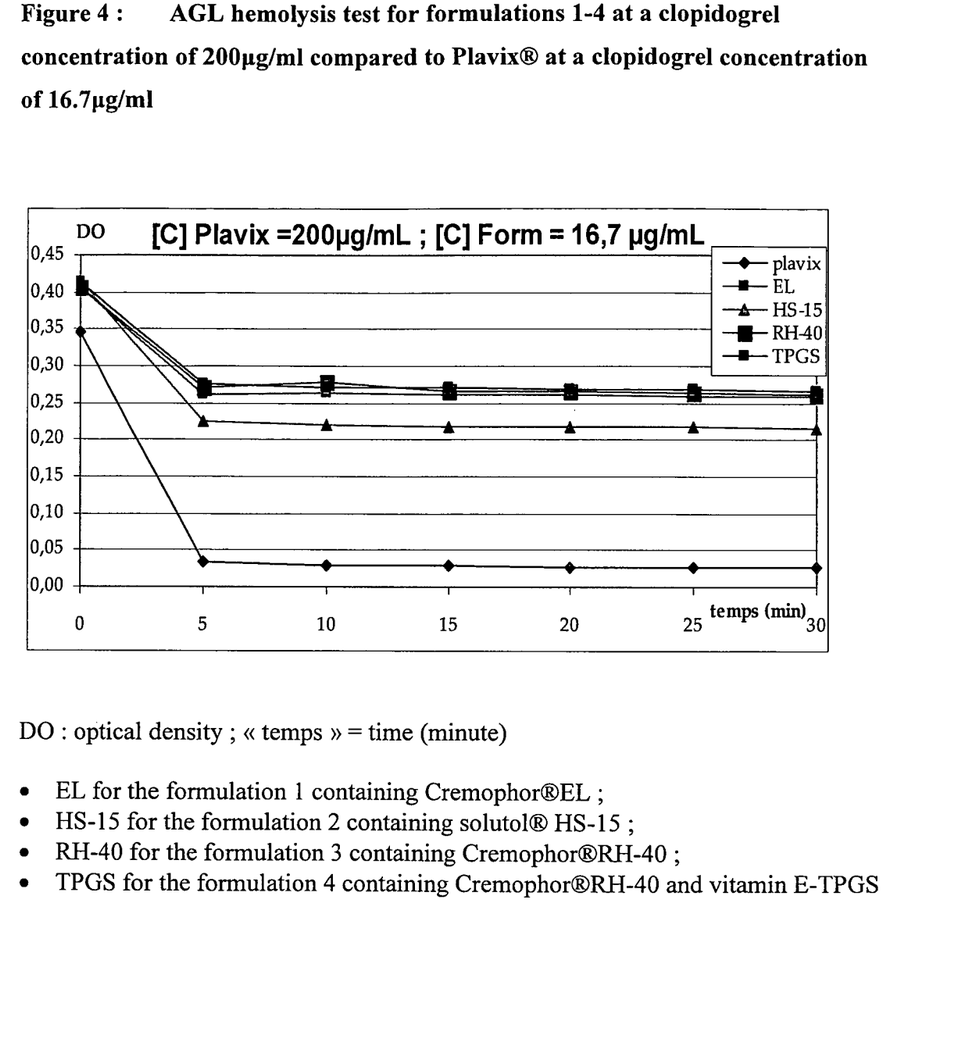
FIG. 4 corresponds to the same test as that of FIG. 1, with a concentration of clopidogrel of 16.7 µg/ml for Plavix® whereas that of formulations 1 to 4 of the Invention was increased to 200 µg/ml.

As described previously, an aliquot of 20 µl of blood is mixed to PBS buffer and to either a solution of Plavix® at clopidogrel concentration of 16.7 µg/ml; or to one of formulations 1 to 4 at a clopidogrel concentration of 200 µg/ml. Each test is duplicated. Results are presented in FIG. 4. We noticed that a very important hemolysis in case of Plavix® (loss of OD higher than 50%) whereas it is much reduced (ranging between 29% and 47%) for formulations 1 to 4 according to the Invention, and this even for high clopidogrel concentrations (200 µg/ml).

EXAMPLE 2

Dissolution Test. Comparison Between the Formulations of the Invention and Plavix®

The dissolution and solubility of formulations 5 to 8 of the Invention (Table 2) were evaluated in comparison to those of Plavix® in simulated intestinal fluids FeSSIF and FaSSIF.

TABLE 2

Formulations 5 to 8 according to the Invention

| Formulation | Clopidogrel free base (mg) | Hydrophilic non ionic surfactant (name; mg) | | Total amount (mg) |
|---|---|---|---|---|
| 5 | 75 | Cremophor ® EL | 290 | 365 |
| 6 | 75 | Solutol ® HS-15 | 290 | 365 |
| 7 | 75 | Cremophor ® RH-40 | 290 | 365 |
| 8 | 75 | Cremophor ® RH-40 Vitamin E/TPGS | 287 3 | 365 |

The fluids FaSSIF (Fasted Simulated Intestinal Fluid) and FeSSIF (Fed Intestinal Simulated Fluid) are described in J. B. Dressman [Oral examination Drug Absorption, Drugs and the Pharmaceutical Sciences (2000)—vol 106].

Method

An amount of 0.5 g of each formulation is added to 1 ml of simulated intestinal fluid; the mixture is incubated at 37° C. after homogenization. A dilution at $1/100^{th}$ is carried out in the mobile phase before to be injected into a HPLC (Perkin Elmer) column #115. For Plavix®, 3 tablets are introduced into 1 ml of medium.

Dissolution in FaSSIF Fluid at 37° C.

The fluid FaSSIF contains 3.9 g of monopotassique phosphoric acid, 1.6 g of sodium taurocholate, 0.6 g of lecithin, 7.7 g of potassium chloride and is completed to 1 liter with distilled water; the pH is adjusted to 6.5 with NaOH.

Figure 5:
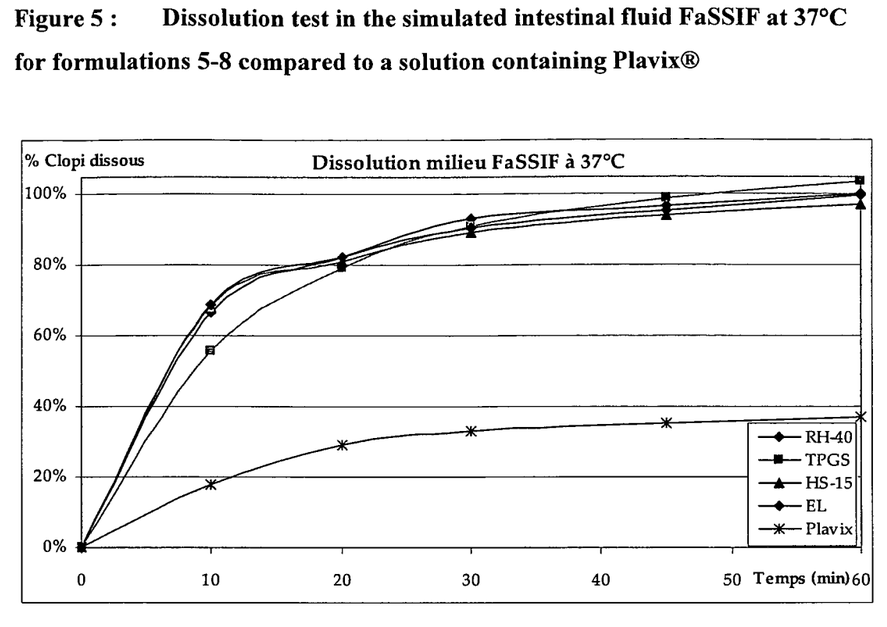
FIG. 5 shows a dissolution test in the FaSSIF fluid comparing formulations 5 to 8 of the Invention with Plavix®.

The results are presented in FIG. 5. We can observe that only 37% of the clopidogrel contained in Plavix® is dissolved, whereas almost the totality (97%) is dissolved after 30 minutes for formulations 5 to 8. In addition, all the 4 formulations of the Invention behave similarly so the choice of hydrophilic non ionic surfactant appears not to be crucial in FaSSIF fluid.

Dissolution in FeSSIF Fluid at 37° C.

The fluid FeSSIF contains 8.7 g of acetic acid, 8.1 g of sodium taurocholate, 2.8 g of lecithin, 15.2 g of potassium chloride, completed to 1 litre with distilled water; the pH is adjusted to 5 with NaOH.

Figure 6:
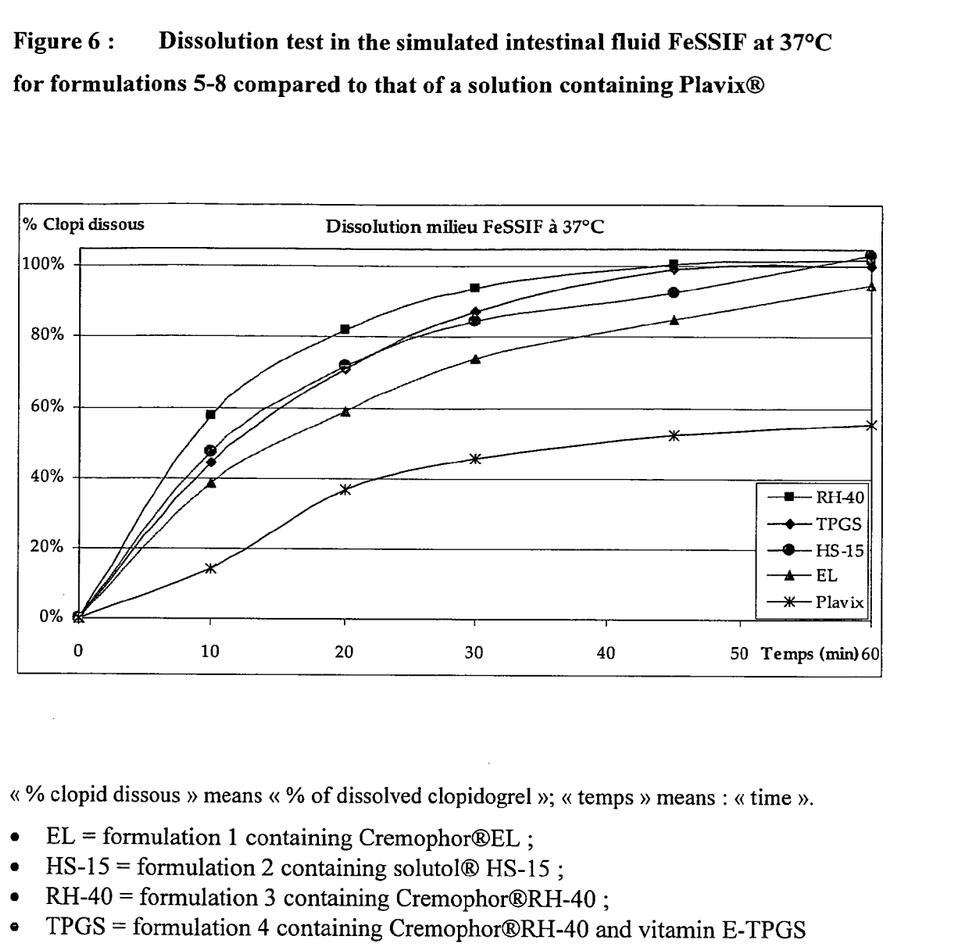
FIG. 6 shows a dissolution test in the FeSSIF fluid comparing formulations 5 to 8 of the Invention with Plavix®.

The results are presented in FIG. 6. We can observe that, after 1 hour, less than 56% of the clopidogrel contained in Plavix® is dissolved, whereas almost the totality (94%) is dissolved in formulations 5 to 8.

From these experiments, we can conclude that the dissolution is improved in both fasted and fed simulated intestinal fluids.

EXAMPLE 3

Solubility Test. Comparison Between the Formulations of the Invention and Plavix®

The objective was to determine whether the solubility of clopidogrel free base—which is almost null in water—, is notably improved for the formulations of the Invention in comparison to Plavix® (which is in the form of salt). This parameter constitutes one element to take in account when bioavailability is to improve.

These tests were carried out at saturation of clopidogrel in a simulated intestinal fluid (such as defined in the US Pharmacopeia SP XXI) at a pH of 7.5 and at 37° C., according to the previous protocol. The results are shown in the following Table 3. The intestinal medium contained 6.8 g of $KH_2PO_4$ in 1 litre of distilled water; the pH is adjusted to 7.5 with KOH.

TABLE 3

Solubility test for formulations 5 to 8 compared to Plavix ®

| Formulation | Hydrophilic non ionic surfactant (name; mg) | Solubility (mg/ml) |
|---|---|---|
| 5 | Cremophor ® EL | 79.9 |
| 6 | Solutol ® HS-15 | 72.5 |
| 7 | Cremophor ® RH-40 | 84.4 |
| 8 | Cremophor ® RH-40 Vitamin E/TPGS | 83 |
| Plavix ® | none | 33.4 |

According to these results, we observe that in the intestinal fluid at pH 7.5 the solubility of clopidogrel is low (33 mg/ml) for Plavix®, whereas the one of formulations 5 to 8 is increased (more than 2 fold). This improved solubility is essentially similar for all formulations 5 to 8.

EXAMPLE 4

Measurement of pH. Comparison Between the Formulations of the Invention and Plavix®

The pH of formulations 5 to 8 was measured in order to evaluate their potential to induce acidity in aqueous medium in comparison to the marketed form of clopidogrel Plavix®. During these tests, each formulation 5 to 8 or a tablet of Plavix® is dissolved in 100 ml of water at 20° C. The results are presented in the following Table 4.

TABLE 4

Measurement of pH for formulations 5 to 8 in comparison to Plavix ®

| Formulation | Hydrophilic non ionic surfactant (name; mg) | pH in 100 ml of water at 20° C. (+/−0, 1) |
|---|---|---|
| 5 | Cremophor ® EL | 5.1 |
| 6 | Solutol ® HS-15 | 5.2 |
| 7 | Cremophor ® RH-40 | 5.3 |
| 8 | Cremophor ® RH-40 + Vitamin E/TPGS | 5.2 |
| Plavix ® | None | 2.6 |

According to these results, it is noted that formulations of the Invention induce a pH physiologically closed to the neutrality (between 5 and 6.1) in contrast to Plavix® which induces an acidic pH (less than 3). This constitutes a significant advantage for oral formulations.

The invention claimed is:

1. An oral, non-hemolytic, oily liquid, pharmaceutical formulation comprising the oily liquid, free base form of clopidogrel, as an antiplatelet agent, dissolved in at least one hydrophilic non-ionic surfactant selected from the group consisting of macrogolglycerol ricinoleate, macrogolglycerol hydroxystearate, macrogol 15 hydroxystearate, and a mixture of macrogolglycerol hydroxystearate and vitamin E/polyethylene glycol succinate, said formulation having a pH close to neutrality after dilution in water, lacking of food effect and without gastric irritation, and the solubility of the clopidogrel in the formulation is greater than 70 mg/ml in a simulated intestinal fluid according to the pharmacopeia USP XXI at pH 7.5 and at 37° C.

2. An oral, non-hemolytic, oily liquid, pharmaceutical formulation comprising the oily liquid, free base form of clopidogrel, as an antiplatelet agent, dissolved in at least pure hydrophilic non-ionic surfactant selected from the group consisting of macrogolglycerol ricinoleate, macrogolglycerol hydroxystearate, macrogol 15 hydroxystearate, and a mixture of macrogolglycerol hydroxystearate and vitamin E/polyethylene glycol succinate, said formulation having a pH close to neutrality after dilution in water, lacking of food effect and without gastric irritation, and the dissolution of the clopidogrel in the formulation is greater than 95% in the simulated digestive fluids FeSSIF or FaSSIF within 30 minutes at 37° C. and under agitation of 50 rpm.

3. The pharmaceutical formulation according to claim 1, further comprising at least one of an antioxidant or a preservative.

4. The pharmaceutical formulation according to claim 2, further comprising at least one of an antioxidant or a preservative.

5. A capsule comprising a pharmaceutical formulation according to claim 1, wherein said clopidogrel is present in an amount of from 5 to 600 mg.

6. The capsule according to claim 5, wherein the clopidogrel is present in an amount of 300 mg.

7. The capsule according to claim 5, wherein the clopidogrel is present in an amount of 75 mg.

8. The capsule according to claim 5, wherein the formulation comprises at least one hydrophilic non ionic surfactant selected from the group consisting of macrogolglycerol hydroxystearate, macrogol 15 hydroxystearate, macrogolglycerol ricinoleate and a mixture of macrogolglycerol hydroxystearate and vitamin E/polyethylene glycol succinate in an amount of from 250 mg to 600 mg.

9. The capsule according to claim 8, wherein the formulation comprises 75 mg of clopidogrel and either 290 mg of macrogolglycerol hydroxystearate, or 287 mg of macrogolglycerol hydroxystearate associated with 3 mg of vitamin E/polyethylene glycol succinate.

10. The capsule according to claim 5, wherein the capsule is made of soft or hard gelatine or of HMPC.

11. The capsule according to claim 5, wherein the capsule is of size 1.

12. A method of preparing the pharmaceutical composition according to claim 1, comprising:
   (a) heating the at least one hydrophilic non ionic surfactant at a temperature of 30° C. to 60° C.;
   (b) dissolving the oily liquid, free base form of clopidogrel in the heated at least one surfactant under agitation at a temperature of 30° C. to 60° C.

13. A method of preparing the capsule according to claim 5, comprising:
   (a) heating the at least one hydrophilic non ionic surfactant to a temperature of 30° C. to 60° C.;
   (b) dissolving the oily liquid, free base form of clopidogrel in the heated at least one surfactant under agitation at a temperature of 30° C. to 60° C.;
   (c) optionally cooling the mixture of step (b) to room temperature and then additionally optionally heating the mixture of step (b) to a temperature of 30° C. to 45° C.; and
   (d) transferring the mixture into the capsule.

14. A method of treating an atherothrombotic pathology comprising administering a pharmaceutical composition according to claim 1, to a person in need of said treatment.

15. The method according to claim 14 wherein the person experiences undesirable effects when administered current antiplatelet drugs.

16. The method according to claim 15 wherein the undesirable effects are related to hemolysis.

17. The method according to claim 15 wherein the undesirable effects are related to gastric acidity when the antiplatelet agent is used under the salt form.

18. The method of claim 14, where in the person is defective in the glucose-6-phosphate dehydrogenase (G6PD), or experiences hematologic disorders.

19. The method of claim 14, wherein the person experiences ulcer gastroduodenal ulcer or gastrointestinal bleedings.

20. A capsule comprising a pharmaceutical formulation according to claim 2, wherein said clopidogrel is present in an amount of from 5 to 600 mg.

21. The capsule according to claim 20, wherein the clopidogrel is present in an amount of 300 mg.

22. The capsule according to claim 20, wherein the clopidogrel is present in an amount of 75 mg.

23. The capsule according to claim 20, wherein the formulation comprises at least one hydrophilic non ionic surfactant selected from the group consisting of macrogolglycerol hydroxystearate, macrogol 15 hydroxystearate, macrogolglycerol ricinoleate and a mixture of macrogolglycerol hydroxystearate and vitamin E/polyethylene glycol succinate in an amount of from 250 mg to 600 mg.

24. The capsule according to claim 23, wherein the formulation comprises 75 mg of clopidogrel and either 290 mg of macrogolglycerol hydroxystearate, or 287 mg of macrogolglycerol hydroxystearate associated with 3 mg of vitamin E/polyethylene glycol succinate.

25. The capsule according to claim 20, wherein the capsule is made of soft or hard gelatine or of HMPC.

26. The capsule according to claim 20, wherein the capsule is of size 1.

27. A method of treating an atherothrombotic pathology comprising administering a pharmaceutical composition according to claim 2, to a person in need of said treatment.

28. The method according to claim 27 wherein the person experiences undesirable effects when administered current antiplatelet drugs.

29. The method according to claim 28 wherein the undesirable effects are related to hemolysis.

30. The method according to claim 28 wherein the undesirable effects are related to gastric acidity when the antiplatelet agent is used under the salt form.

31. The method of claim 27, where in the person is defective in the glucose-6-phosphate dehydrogenase (G6PD), or experiences hematologic disorders.

32. The method of claim 27, wherein the person experiences ulcer gastroduodenal ulcer or gastrointestinal bleedings.

33. A method of preparing the pharmaceutical composition according to claim 2, comprising:
   (a) heating the at least one hydrophilic non ionic surfactant at a temperature of 30° C. to 60° C.;
   (b) dissolving the oily liquid, free base form clopidogrel in the heated at least one surfactant under agitation at a temperature of 30° C. to 60° C.

34. A method of preparing the capsule according to claim 20, comprising:
   (a) heating the at least one hydrophilic non ionic surfactant to a temperature of 30° C. to 60° C.;
   (b) dissolving the oily liquid, free base form clopidogrel in the heated at least one surfactant under agitation at a temperature of 30° C. to 60° C.;
   (c) optionally cooling the mixture of step (b) to room temperature and then additionally optionally heating the mixture of step (b) to a temperature of 30° C. to 45° C.; and
   (d) transferring the mixture into the capsule.

\* \* \* \* \*